US00PP28767P3

(12) United States Plant Patent
Bean

(10) Patent No.: US PP28,767 P3
(45) Date of Patent: Dec. 12, 2017

(54) ***AGAPANTHUS* HYBRID PLANT NAMED 'AMDB002'**

(50) Latin Name: ***Agapanthus* hybrid**
Varietal Denomination: AMDB002

(71) Applicant: Quinton Bean, Johannesburg (ZA)

(72) Inventor: Quinton Bean, Johannesburg (ZA)

( * ) Notice: Subject to any disclaimer, the term of this patent is extended or adjusted under 35 U.S.C. 154(b) by 0 days.

(21) Appl. No.: 15/330,691

(22) Filed: Oct. 27, 2016

(65) Prior Publication Data

US 2017/0127596 P1 May 4, 2017

Related U.S. Application Data

(60) Provisional application No. 62/250,025, filed on Nov. 3, 2015.

(51) Int. Cl.
*A01H 5/02* (2006.01)

(52) U.S. Cl.
USPC ..... Plt./398

(58) Field of Classification Search
USPC ..... Plt./398
See application file for complete search history.

*Primary Examiner* — Annette H Para
(74) *Attorney, Agent, or Firm* — Samuel R. McCoy, Jr.

(57) ABSTRACT

A new cultivar of *Agapanthus*, 'AMDB002', that is characterized by a vigorous growth habit, a medium plant size, inflorescences that form dense umbels of flowers, violet-blue outer tepal color, violet-blue and white striping of the inner tepal, an extended flowering season with blooming and re-blooming from early spring to late summer and sporadically in early fall, a very floriferous blooming period producing an unusually high number of inflorescences, and good resistance to fungal infection from *Macrophoma agapanthii.*

2 Drawing Sheets

Latin name of the genus and species: The Latin name of the novel variety disclosed herein is *Agapanthus* hybrid.

Variety denomination: The inventive variety of *Agapanthus* hybrid disclosed herein has been given the variety denomination 'AMDB002'.

BACKGROUND OF THE INVENTION

The present invention relates to a new and distinct variety of *Agapanthus* hybrid, which has been named 'AMDB002'. Its market class is PLT/398. *Agapanthus*, commonly called "lily of the Nile", is a flowering perennial native to South Africa that forms clumps of dark green strap-like leaves with umbels rising above the foliage and bearing numerous flowers which range in color from pale violet to dark purple. Its consistent size and performance, combined with its attractive inflorescences through its hardiness range make it an ideal choice for specimen, borders and mass plantings in any full to filtered sun to shady, low-maintenance landscape or container.

Parentage: The cultivar 'AMDB002' is a seedling selection resulting from a controlled pollination breeding program by the Inventor in Hartebeespoort, Northwest Province, South Africa. The objective of the breeding program is to develop new cultivars of *Agapanthus* that are fast growing, early flowering and that display repeat flowering and unique flower colors. The Inventor made a controlled cross in October of 2008 between an unnamed plant of *Agapanthus comptonii* hybrid from the Inventor's breeding program as the female parent and an unnamed plant of *Agapanthus campanulatus* hybrid from the Inventor's breeding program as the male parent. The Inventor selected 'AMDB002' in November of 2010 as a single unique plant amongst the seedlings that resulted from the above cross.

Asexual Reproduction: Asexual propagation of the new cultivar was first accomplished by division by the Inventor in Hartebeespoort, Northwest Province, South Africa in November of 2010. Asexual propagation by division and tissue culture through six successive generations has determined that the characteristics of the new cultivar are stable and are reproduced true to type in successive generations.

SUMMARY OF THE INVENTION

The following traits have been repeatedly observed and represent the characteristics of the new cultivar. The characteristics in combination distinguish 'AMDB002' as a distinct cultivar of *Agapanthus.*

1. 'AMDB002' exhibits a fast growing and fast multiplying growth habit.
2. 'AMDB002' exhibits a medium plant size.
3. 'AMDB002' exhibits inflorescences that form dense umbels of flowers that are violet-blue in color.
4. 'AMDB002' exhibits an extended flowering season blooming and re-blooming from early spring to late summer and sporadically in early fall.
5. 'AMDB002' exhibits a very floriferous blooming period producing an unusually high number of inflorescences.
6. 'AMDB002' exhibits good resistance to fungal infection from *Macrophoma agapanthii.*

DETAILED BOTANICAL DESCRIPTION OF THE VARIETY

Figure 1:
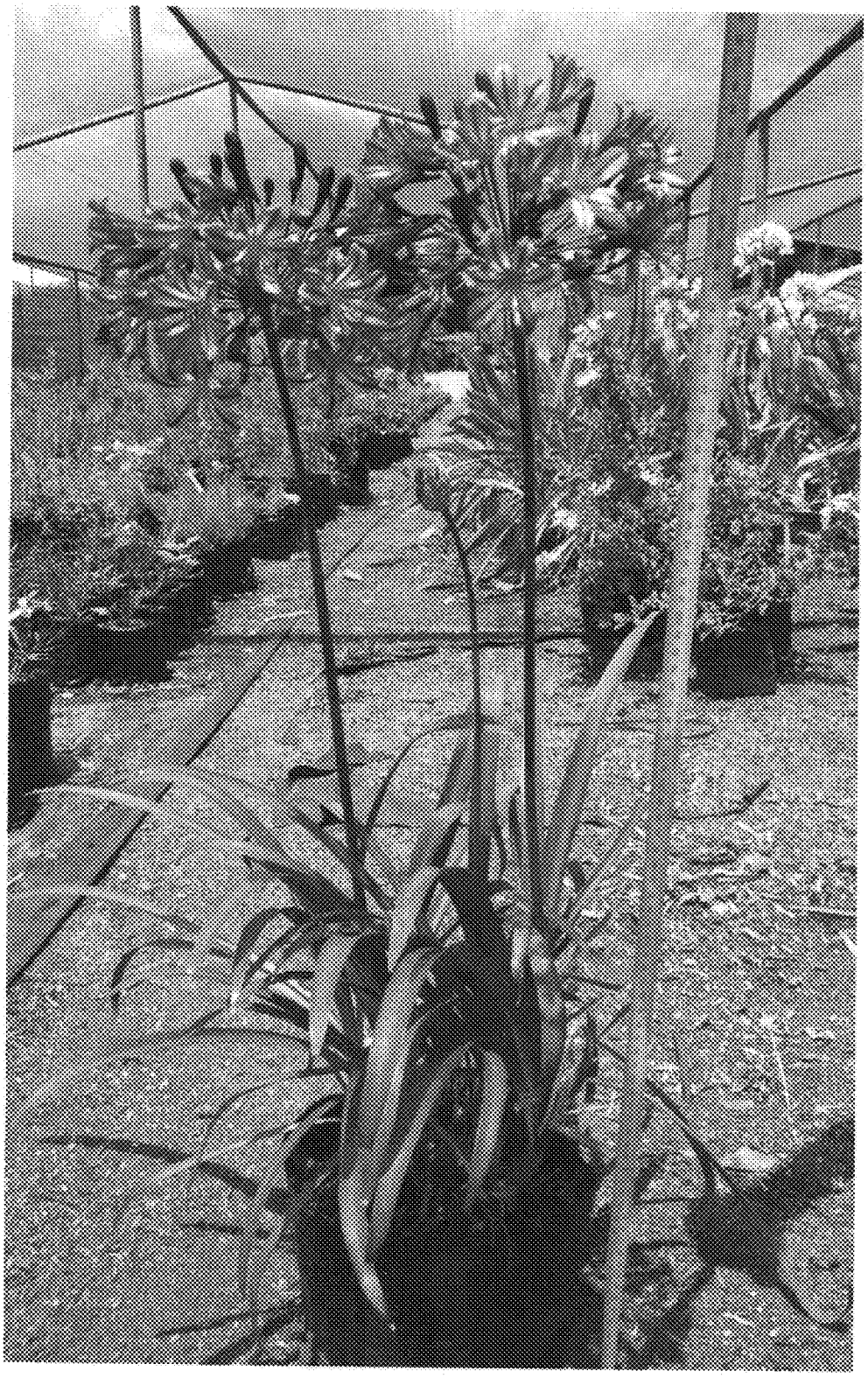
FIG. 1 shows as true as is reasonably possible to obtain in color photographs of this type, an exemplary 'AMDB002' specimen, approximately 24 months of age, grown at a wholesale nursery in Hartebeespoort, Northwest Province, South Africa under 40 percent shade.
Figure 2:
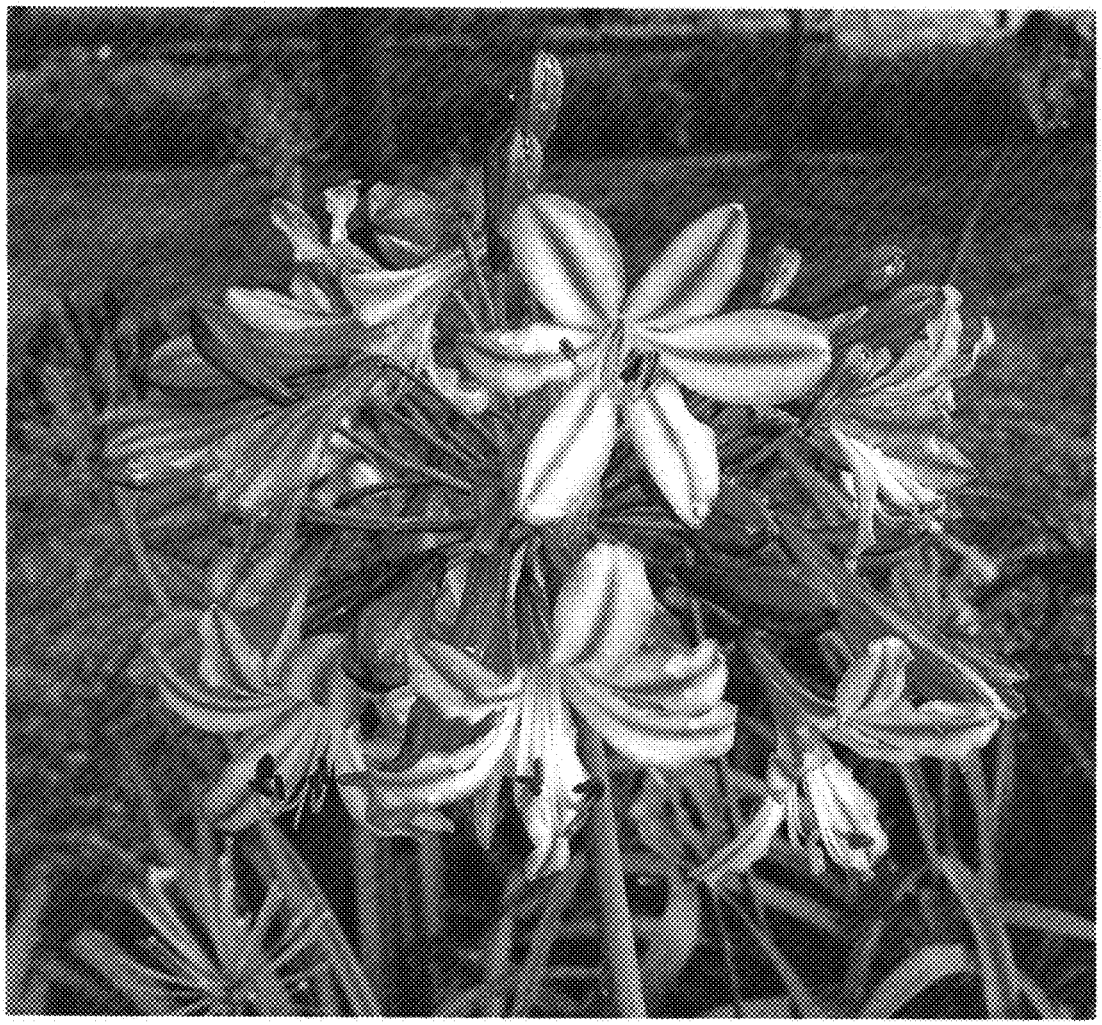
FIG. 2 shows as true as is reasonably possible to obtain in color photographs of this type, an exemplary umbel of 'AMDB002'.

The following is a detailed botanical description of a new and distinct *Agapanthus* hybrid seedling selection known as 'AMDB002'. Unless indicated otherwise, the descriptions disclosed herein are based upon observations made in October 2015 of mature 'AMDB002' plants, approximately 24 months of age, grown outdoors at a wholesale nursery facility in Hartebeespoort, Northwest Province, South Africa. Said plants were grown under 40 percent shade cloth, irrigated manually as needed, and fertilized every four months with a slow release complete fertilizer. Preventative pesticide applications were made every three to four weeks.

Those skilled in the art will appreciate that certain characteristics will vary with older or, conversely, with younger plants. 'AMDB002' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 1986 edition. Note that generic color descriptions such as "green" do not exist in the R.H.S. charts and the corresponding R.H.S. colors are quoted.

The distinguishing features and other characteristics of *Agapanthus* hybrid 'AMDB002' are apparent from the description provided below.

General plant description:

- *Plant habit*.—Rhizomatous herbaceous perennial with an arching habit.
- *Height*.—40 to 50 cm.
- *Width*.—70 to 80 cm.
- *Bloom period*.—AMDB002 exhibits an extended flowering season, blooming and re-blooming from early spring to late summer and sporadically in early fall.
- *Hardiness*.—USDA Zone 9 to 10.
- *Environmental tolerances*.—Prefers to be grown in filtered sun. Drought tolerant once established; moderate to good recovery with watering after severe wilting. Tolerates a wide range of soil types from sandy loam to loamy clay.
- *Pest and disease susceptibility or resistance*.—'AMDB002' exhibits good resistance to fungal infection from *Macrophoma agapanthii*.
- *Propagation*.—Propagation is accomplished through division of rhizomes and also meristem tissue culture.
- *Time to initiate roots*.—Approximately 3 weeks.
- *Crop time*.—Depending on latitude of and microclimate of growing location, a fully rooted cutting requires approximately 3 months with an additional 5 to 7 months needed to produce a mature and marketable 15 cm container.

Roots: The roots are fibrous and freely-branched, colored white, fleshy, similar to other *Agapanthus*; high root density.

Stem:

- *Branching habit*.—Acaulescent, rhizomatous plant with shoots emerging from rhizomes with an upright attitude.

Basal shoots:

- *Shoots density*.—15 divisions, or propagules, per nursery pot, with the oldest propagules near the center of the plant's crown possessing 12 to 14 leaves and shoots of varying ages and sizes.
- *Shoot strength*.—Medium.
- *Cross section*.—Concave.
- *Shoot color* (*adaxial* & *abaxial surfaces*).—Nearest to yellow-green RHS 144A to 144B.
- *Shoot surface texture*.—Smooth.

Foliage:

- *Type*.—Evergreen.
- *Arrangement*.—Basal.
- *Division*.—Simple.
- *Attitude*.—Arched.
- *Shape*.—Linear.
- *Apex*.—Acute.
- *Base*.—Sheathed.
- *Cross section*.—Flat.
- *Venation*.—Parallel.
- *Vein color* (*adaxial surfaces*).—Green, RHS 137A.
- *Vein color* (*abaxial surfaces*).—Green, RHS 137C.
- *Margins*.—Entire.
- *Attachment*.—Acaulescent.
- *Texture*.—Smooth and glossy.
- *Surface hairiness* (*adaxial surface*).—Glabrous.
- *Surfaces hairiness* (*abaxial surface*).—Glabrous.
- *Mature leaf dimensions*.—Longest observed leaf measuring length 280 mm, average width 20 mm at widest point.
- *Mature leaf color, adaxial* & *abaxial surfaces*.—Green, approximating to a combination of RHS 137A to 137B, and Green RHS 137C, respectively.
- *Petiole*.—Leaves are acaulescent; sessile.
- *Stipules*.—Absent.

Inflorescence:

- *Inflorescence type*.—Umbellate.
- *Umbel diameter*.—Approximately 180 to 200 mm.
- *Number of umbels per pot*.—Potentially more than one inflorescence per propagule, per growing season.
- *Number of flowers per umbel*.—Approximately 55 to 60.
- *Scape dimensions*.—Approximately 50 to 55 cm long and 1.0 to 1.25 cm wide at the base.
- *Other characteristics of scape*.—Color is Green RHS 137D; cylindrical shape; texture is smooth; glabrous.

Buds:

- *Bud shape*.—Obelliptic; apex round; base cuneate.
- *Bud dimensions*.—28 mm long and 7 mm wide, prior to anthesis.
- *Bud color*.—Violet-Blue RHS 93A.
- *Bud texture*.—Glabrous.

Flowers:

- *General*.—Apetalous flowers; shape is campanulate to rotate; self-cleaning and non-fragrant. Attitude is upward and outward.
- *Pedicel dimensions*.—38 to 40 mm long and 1.5 mm wide, as measured.
- *Pedicel color*.—Green RHS 137D at the base and darker at and near the distal end, near Yellow-Green RHS 147A.
- *Pedicel surface*.—Glabrous.

*Perianth dimensions*.—Approximately 40 to 45 mm wide and 30 mm deep, at anthesis.
*Tepals*.—Six basally fused tepals.
*Tepal shape*.—Oblanceolate; apex is round.
*Tepal dimensions*.—28 mm long and 19 mm wide, as measured.
*Outer tepal color*.—Ranging from Violet-Blue RHS 94B to 94C.
*Inner tepal color*.—Margins — Ranging from Violet-Blue RHS 92C to Violet-Blue RHS 94D. Midrib area — Violet-Blue RHS 92C. Intermediate area — Violet-Blue RHS 92D.
*Tepal surface*.—Smooth; glabrous.
*Tepal margin*.—Entire.

Reproductive organs:
*Stamens*.—Six.
*Stamen attachment*.—Each is adnate to a corresponding tepal.
*Filament color*.—Violet-Blue RHS 92D at base, becoming Violet-Blue RHS 92C near apex.
*Filament dimensions*.—17 mm long and approximately 0.75 mm wide.
*Anther attachment*.—Dorsifixed.
*Anther dimensions*.—1.5 mm long and 1 to 1.25 mm wide.
*Anther color*.—Appearing as a mixture of Black RHS 202A and Green-yellow RHS 1B.
*Pollen*.—Present; high quantity; color appears to be Green-Yellow RHS 1B.
*Pistil*.—One.
*Pistil dimensions*.—21 mm long, from apex of ovary; width is approximately 0.75 mm.
*Pistil color*.—Violet-Blue RHS 92D at base, becoming Violet-Blue RHS 92C near apex.
*Ovary shape*.—Oblong.
*Ovary color*.—Yellow-Green RHS 150B.
*Ovary dimensions*.—7 mm long and 3.5 mm wide.
*Ovary position*.—Superior.

Fruit and seeds: Not observed.

Comparisons With The Parents

The new *Agapanthus* plant 'AMDB002' may be distinguished from the female parent by the following combination of characteristics:

1. 'AMDB002' exhibits a larger inflorescence when compared to that of the female parent.
2. 'AMDB002' exhibits a larger flower and longer pedicel when compared to that of the female parent.
3. 'AMDB002' exhibits an improved reblooming habit when compared to that of the female parent.

The new *Agapanthus* plant 'AMDB002' may be distinguished from the pollen parent by the following combination of characteristics:

1. 'AMDB002' exhibits a violet-blue outer tepal color, whereas the tepals of the pollen parent exhibit a purple color.
2. 'AMDB002' initiates blooming earlier in the season when compared to the pollen parent.
3. 'AMDB002' exhibits a significantly improved reblooming habit when compared to that of the pollen parent.

Comparisons With Most Similar *Agapanthus* Cultivar Known to the Inventor

The new *Agapanthus* plant 'AMDB002' may be distinguished from the most similar variety known to the breeder, *Agapanthus* 'Andbin' (U.S. Plant Pat. No. 26,336), by the following combination of characteristics:

1. 'AMDB002' exhibits a smaller flower when compared to the flower of 'Andbin'.
2. 'AMDB002' exhibits a campanulate to rotate flower shape with a longer perianth tube, whereas 'Andbin' exhibits an open, rotate flower shape with a shorter perianth tube.
3. The tepals of 'AMDB002' exhibit blue margins and midribs with a white intermediate zone, whereas 'Andbin' exhibits a solid blue tepal coloration.
4. 'AMDB002' exhibits a larger overall plant size when compared to 'Andbin'.

That which is claimed is:

1. A new and distinct *Agapanthus* hybrid plant selection named 'AMDB002', substantially as described and illustrated herein.

* * * * *